(12) United States Patent
Kyle et al.

(10) Patent No.: US 7,958,770 B2
(45) Date of Patent: Jun. 14, 2011

(54) HEATED TRANSFER LINE FOR USE IN HIGH TEMPERATURE MICROWAVE CHROMATOGRAPHY

(75) Inventors: Kevin Kyle, Clute, TX (US); Larry Youngblood, Houston, TX (US)

(73) Assignee: Petroleum Analyzer Company, LP, Houston, TX (US)

( * ) Notice: Subject to any disclaimer, the term of this patent is extended or adjusted under 35 U.S.C. 154(b) by 755 days.

(21) Appl. No.: 11/834,495

(22) Filed: Aug. 6, 2007

(65) Prior Publication Data

US 2009/0038372 A1 Feb. 12, 2009

(51) Int. Cl.
*G01N 30/06* (2006.01)
(52) U.S. Cl. .................................................. 73/23.41
(58) Field of Classification Search ............ 73/23.4, 73/23.41
See application file for complete search history.

(56) References Cited

U.S. PATENT DOCUMENTS

| | | |
|---|---|---|
| 3,169,389 A | 2/1965 | Green, Jr. et al. |
| 3,232,093 A | 2/1966 | Burow et al. |
| 3,516,771 A | 6/1970 | Rendina |
| 3,527,567 A | 9/1970 | Philyaw et al. |
| 4,204,423 A | 5/1980 | Jordan |
| 4,650,964 A * | 3/1987 | Vincent .................. 392/468 |
| 4,728,776 A * | 3/1988 | Vincent .................. 392/480 |
| 4,985,625 A * | 1/1991 | Hurst ...................... 250/288 |
| 5,005,339 A | 4/1991 | Capawana |
| 5,370,529 A | 12/1994 | Lu et al. |
| 5,939,614 A | 8/1999 | Walters et al. |
| 6,029,498 A | 2/2000 | Walters et al. |
| 6,155,212 A | 12/2000 | McAlister |
| 6,182,504 B1 | 2/2001 | Gaisford |
| 6,316,759 B2 | 11/2001 | Gaisford et al. |
| 6,514,316 B1 | 2/2003 | Gaisford et al. |
| 6,762,834 B2 | 7/2004 | Komatani et al. |
| 7,221,861 B1 * | 5/2007 | Hannigan et al. ......... 392/478 |

FOREIGN PATENT DOCUMENTS

DE   10 2004 010 969 A1   9/2005

* cited by examiner

*Primary Examiner* — Daniel S Larkin
(74) *Attorney, Agent, or Firm* — Gunn Lee & Cave, P.C.

(57) ABSTRACT

A heat transfer line assembly is disclosed for microwave heated chromatography instruments. Analytical instruments incorporating a microwave oven including the heated transfer lines are also disclosed as well as methods for making and using same.

51 Claims, 3 Drawing Sheets

HEATED TRANSFER LINE FOR USE IN HIGH TEMPERATURE MICROWAVE CHROMATOGRAPHY

BACKGROUND OF THE INVENTION

1. Field of the Invention

The present invention relates to a heated transfer line assembly for use in the field of liquid and gas chromatography, where the assemblies are adapted to reduce sample condensation in transfer lines leading to and away from a column in a microwave oven and to methods for making and using same.

More particularly, the present invention relates to a heated transfer line assembly for use with liquid and gas chromatography instruments, where the assembly includes a rod having an aperture therethrough adapted to receive a transfer line extending from one end of the rod and terminating near the second end of the rod. The second end of the rod is adapted to receive a lead of a column so that an amount of the column that is unheated is minimized. The assembly also includes a heating element to maintain the transfer line at a desired elevated temperature and a housing surrounding the rod over a portion of its length. The present invention also relates to methods for making and using same and to instruments including the heated transfer line assembly.

2. Description of the Related Art

Gas and liquid chromatography are physical methods for the separation, identification, and quantification of chemical compounds. These methods are used extensively for applications that include the measurement of product purity in analytical chemistry, the detection, measurement and/or determination of environmental contaminants, the detection, measurement, determination and/or characterization of natural substances, and the development of pharmaceuticals.

The fundamental methods used in gas and liquid chromatography to separate chemical constituents are similar. A sample mixture is injected into a flowing neutral carrier stream and the combination then flows through a tube or chromatographic column. The inner surface of the column is coated or the column is packed with a material called the stationary phase. As the sample mixture in the carrier stream flows through the column, the components within the stream partition between the moving phase (the stream) and the stationary phase and are retained by the stationary phase to a greater or lesser degree depending on the relative volatility (in the case of gas chromatography) or the relative solubility (in the case of liquid chromatography) of the individual components and on their respective affinities for the stationary phase. When the individual mixture components are released back into the carrier stream by the stationary phase, they are swept towards the column outlet where they are detected and measured with a detector. Different chemical compounds are retained for different times by the stationary phase. By measuring the retention times, the specific compounds in the mixture can be differentiated and/or identified. The relative concentrations of the compounds are determined by comparing the peak amplitudes measured with the detector for each compound.

The primary difference between gas and liquid chromatography is the mode of separation. In gas chromatography, the sample is volatilized and propelled down the analytical column by a moving stream of gas. In liquid chromatography, the sample is dissolved and propelled down the analytical column in a moving stream of liquid. Another difference between gas and liquid chromatography is that the columns used in liquid chromatography are generally filled or packed with the stationary phase, while those used in gas chromatography can also have the stationary phase coated or bonded to the interior wall, instead.

GC and LC measurements are facilitated by the application of heat to the chromatographic column to change its temperature. The use of a heated column oven in gas chromatographic systems greatly increases the number of compounds that can be analyzed and speeds up the time required for each analysis by increasing the volatility of higher molecular weight compounds. Heating an LC column affects the relative solubility of the mixture's components in the two phases and can enhance the separation as well as improve the repeatability of the elution times of the component chemicals.

Many methods have been described for heating chromatographic columns. The simplest and most commonly used method utilizes resistive heating elements to heat air which is in turn circulated through an insulated oven in which the column is placed. For example, U.S. Pat. No. 3,527,567 to Philyaw et al. describes a GC oven heated with resistive elements.

The resistive element heating method has several limitations. To achieve even heating of the column, a large volume of air is rapidly circulated around the chromatographic column. In addition to heating the column, the air heats the oven itself. Because the thermal mass of the oven is much larger than that of the column, the rate at which the column can be heated is commensurately reduced. A related problem is cooling time. After heating the oven to a high temperature during an analysis, it takes significantly longer to cool the oven plus the column to their initial temperature so that the next sample may be analyzed than it would to cool the column alone. Together, these limitations reduce the throughput of the chromatographic method and instrument.

Attempts to localize the resistive heat element onto the column itself so as to reduce or eliminate peripheral heating of the "oven" are described in U.S. Pat. No. 3,169,389 to Green et al., U.S. Pat. No. 3,232,093 to Burow et al., and in U.S. Pat. No. 5,005,399 to Holtzclaw et al. Each of these patents describe methods for directly wrapping or cladding the chromatographic column with a resistive heating element. Methods are also described for positioning the resulting metal clad column adjacent to a cooling source to decrease cooling times. This method of heating can be difficult to implement in practice because of uneven heating of the column due to local hot or cold spots in the resistive heating element surrounding the column. Uneven heating of the column in turn compromises the quality of the analysis.

Yet another limitation of all resistively heated chromatographic devices is that if operated improperly, they can be driven to temperatures higher than the maximum tolerated by a given column resulting in damage to or destruction of the column.

An alternative method for heating chromatographic columns is microwave heating as described in U.S. Pat. No. 4,204,423 to Jordan. Potential advantages of microwave heating are efficiency and selectivity. Suitable objects placed in a microwave oven will be heated when the oven is operated, but the temperature of the oven itself will not change. Microwave heating occurs in materials which absorb the microwave energy and convert it into heat. Current chromatographic columns are generally made of materials that do not absorb microwave energy at an appreciable rate. For example, most GC capillary columns are made of polyimide and fused silica. Consequently, such columns will not heat at an appreciable rate when placed in a microwave oven. The apparatus taught by Jordan is not practicable with these columns.

U.S. Pat. Nos. 6,514,316, 6,316,759, 6,182,504, 6,093,921, 6,029,498, and 5,939,614, incorporated herein by reference, disclose various aspect of microwave heating in GC and LC applications. These microwave heating techniques are gaining in utility. However, like all other heating system, microwave heating does present certain problems. One problem is associated with transferring material to a column in a microwave heating oven, especially in high temperature applications, where condensation in transfer lines can significantly and adversely affect GC and LC measurements.

Although the microwave heated chromatography instruments are becoming more prevalent even in high temperature applications, condensation problems still persist due to transfer line cooling in the instrument. Thus, there is a need in the art for transfer lines that reduce and/or substantially eliminate sample component condensation as a sample progresses into and out of a microwave heated column.

SUMMARY OF THE INVENTION

The present invention provides a heated transfer line apparatus including a high thermal conductivity member having an aperture therethrough. The member is adapted to receive a transfer line extending from a first end to a location near a second end of the member, where the second end of the member is designed to receive a column end. The apparatus also includes a heating element for maintaining the member and the transfer line at an elevated temperature, where the elevated temperature is sufficient to maintain all components in the sample in their vapor or gas phase. The temperature is generally the minimum vaporization temperature of the sample. The apparatus also includes a housing surrounding a portion of the member. The apparatus is designed to be inserted into the oven so that an unheated portion of column is less than a critical distance or the unheated portion is sufficiently small to reduce or eliminate sample condensation in the unheated portion of the column.

The present invention also provides an oven apparatus including a housing having a microwave heating assembly, a chromatographic column including an inlet and outlet and two heated transfer line assemblies. The inlet and outlet of the column are designed to be inserted into ends of the transfer line assemblies so that unheated portions of the column at the inlet and outlet are each less than or equal to a critical distance. The heated transfer lines are designed to be heated to an elevated temperature, where the temperature is sufficient to maintain all sample components in their vapor or gas phase and to maintain a substantially uniform temperature profile along a length of the transfer line, where the term substantially uniform temperature profile means that the temperature across the profiles varies from a set temperature by no more than ±20° C. In certain embodiments, the substantially uniform temperature means that the temperature varies by no more than ±15° C. In certain embodiments, the substantially uniform temperature means that the temperature varies by no more than ±10° C. In certain embodiments, the substantially uniform temperature means that the temperature varies by no more than ±5° C. The assemblies are designed to extend into the oven an amount sufficient to maintain the unheated portion of the column leads below the critical distance, but insufficient to interfere with the microwave field generated in the microwave oven.

The present invention also provides a microwave heated chromatography instrument including a sample delivery assembly. The instrument also includes an oven apparatus including a housing having a microwave heating assembly, a chromatographic column including an inlet and an outlet and two heated transfer line assemblies, one assembly having an end adapted to receive an inlet and one assembly having an end adapted to receive the outlet. The assemblies extend into the oven an amount sufficient to receive the inlet and outlet of the column, but insufficient to interfere with a microwave field generated by the microwave heating assembly in the housing to heat the column. The assemblies are positioned in the housing so that a length of exposed column is minimized. In certain embodiments, the length is less than or equal 5 mm, 5 mm or less. The instrument also includes a detector/analyzer assembly, which may include oxidation subassemblies and/or reduction subassemblies.

The present invention also provides a method for increasing reliability of microwave heated chromatography instruments including the step of providing an instrument of this invention. The method also includes the step of maintaining an input transfer line and an inlet lead portion of a chromatography column at an elevated temperature sufficient to completely maintain the sample in a vaporized state between the sample delivery assembly and the oven assembly, where the assembly has an end designed to receive an inlet lead of the column. The method can also include the step of maintaining an output transfer line and an outlet lead portion of the column at an elevated temperature sufficient to maintain an uniform heating profile in the section of the instrument that connects the oven to the detector/analyzer assembly or to an optional assembly between the heating assembly and the optional assembly.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

The inventors have found that a transfer line assembly can be constructed for use in microwave heated chromatography instruments, especially for use in high temperature applications. Microwave heated chromatography instruments, especially those used in high temperature applications, are severely impacted by inlet temperature, which adversely affects repeatability and reproducibility of measured chromatographic data. The inventors have found that it is advantageous to maintain the inlet or injector at a temperature sufficient to completely vaporize a sample being injected into the instrument or forwarded to the instrument from a sample loop. The inventors have also found that it is advantageous, but to a lesser degree, to maintain an uniform heating profile in a section of the instrument that connects the oven to the detector or other instrument component. The inventors have found that the heated transfer line assemblies are necessary to maintain a minimum vaporization temperature uniformly throughout a length of the transfer line from an injector or a sample loop to a column inlet lead. If the transfer line is not uniformly heated and maintained at the minimum vaporization temperature, the sample or sample component can condense in the line or at the inlet to the column, leading to poor reproducibility and sometimes even to the inability to make a complete measurement. The inventors have also found that in microwave heated chromatography instruments there is a critical length of unheated column leads that can be tolerated without adversely affecting instrument performance. Generally, the critical length of unheated column lead is no more than 5 mm ($\leqq 5$ mm). In certain embodiments, the critical length or distance is no more than 4 mm. In other embodiments, the critical length or distance is no more than 3 mm. In other embodiments, the critical length or distance is no more than 2 mm. In other embodiments, the critical length or distance is no more than 1 mm. In fact, the inventors have found that high temperature chromatography using microwave heating is not achievable without the use of the heated transfer line assemblies of this invention.

The present invention broadly relates to a heated transfer line apparatus including a housing including a proximal end cap, a distal end cap, a middle section, a proximal tubular member, and a distal tubular member, where the end caps fit on to the middle section to form an enclosed insulated zone, the proximal tubular member extends from the proximal end cap forming a first end of the apparatus and having a fitting adapted to connect to a sample introduction unit. The apparatus also includes an elongated member including a first end, a tapered second end and an aperture therethrough, where the elongated member is disposed inside the proximal tubular member, the middle section, and the distal tubular member and extends out of the distal tubular member so that the second end of the elongated member forms a second end of the apparatus. The apparatus also includes a transfer line extending from the fitting of the first end of the apparatus to a location near the second end of the apparatus. The apparatus also includes a heating element surrounding the elongated member from the proximal end cap to the distal end of the distal tubular member and adapted to maintain the member and the transfer line at an elevated temperature having a temperature difference across the apparatus of less than a minimum temperature difference, where the elevated temperature is sufficient to maintain all components in a sample passing through the transfer line in their vapor or gas phase. The tapered second end is adapted to be inserted into a microwave oven including a chromatography column and to receive a column end or column lead so that an unheated portion of the column is sufficiently small to reduce or eliminate sample condensation in the unheated portion of the column.

The present invention also broadly relates to an oven apparatus including a housing including a microwave heating assembly and a microwave heated zone, a chromatographic column disposed inside the microwave heated zone and including an inlet and outlet, and two heated transfer line assemblies extending into the housing and adapted to receive the outlet and inlet so that there is no more than a critical distance of unheated column at either its outlet end or its inlet end as described above.

The present invention also broadly relates to a microwave heated chromatography instrument including a sample delivery assembly, an oven apparatus, as described above, connected to the sample delivery assembly, and a detector/analyzer assembly connected to the distal end of the second transfer line and designed to detect and analyze components of the sample.

The present invention also broadly relates to a method for increasing reliability of microwave heated chromatography instruments including the step of providing an instrument of this invention. The method also includes the step of maintaining the first transfer line at a first elevated temperature sufficient to maintain the sample in a vaporized state between the sample delivery assembly and the oven assembly having a first temperature difference of no more that $\pm 20°$ C. The method also includes the step of maintaining the second transfer line at a second elevated temperature sufficient to maintain the separated sample components in a vaporized state between the oven and the detector having a second temperature difference of no more that $\pm 20°$ C. The method also includes the step of detecting/analyzing the sample components. The method can also include the step of oxidizing the sample components to their corresponding oxides prior to detection and analysis. The method can also include the steps of oxidizing the sample components to their corresponding oxides and reducing a portion of the oxides to their corresponding reduced states prior to detection and analysis.

The heated transfer line assembly broadly includes a transfer tube and a metal rod having an inlet end and an outlet end. The rod has an outer diameter (OD) and an inner diameter (ID). The OD of the rod is sized sufficient for the rod to have a desired heat storage capacity; while the ID is sized to be just large enough to receive a lead of a chromatography column. The transfer tube extends a length of the rod except for the portion designed to receive the column lead or a fitting. When a column lead is inserted into the outlet end of the assembly, the assembly is designed so that an end of the lead will abut the end of the transfer tube. The assembly also includes a heating element for heating and maintaining the rod and transfer line at an elevated temperature. The elevated temperature is sufficient to maintain the transfer line at a temperature above a minimum vaporization temperature of the highest boiling component in the sample. The assembly also includes an insulating housing surrounding the heating element and a portion of the length of the rod. The assembly also includes a temperature controller designed to supply power to the heating element. The assembly is adapted to maintain the transfer line at a temperature, where a temperature difference across the length of the assembly is no more than $\pm 10°$ C. In certain embodiments, the temperature difference across the length of the assembly is no more than $\pm 5°$ C. In certain embodiments, the temperature difference across the length of the assembly is no more than $\pm 2.5°$ C. In certain embodiments, the temperature difference across the length of the assembly is no more than $\pm 1°$ C. In certain embodiment, the metal out of which the rod is made is a metal having a high heat transfer coefficient. In certain embodiments, the ID is about 0.035" inch, but the ID is variable depending on the microwave column being used. The major problem of uniformity is solved due to the excellent thermal conductivity of metal rod and the thermal mass of the tube. The assembly also includes a thermocouple placed approximately at the midpoint of the assembly and serves as feedback for the controller. Optionally, for longevity and power considerations, a zirconium oxide coating is applied over the heating elements. In certain embodiments, the heated transfer line assembly is capable of maintaining a temperature difference of no more than $\pm 1$ to no more than $\pm 10$ C across its length at a set point of 400° C. In certain embodiments, the metal out of which the rod is made is a metal having a high thermal conductivity, which solves the problem of temperature uniformity and maintenance problems due to the thermal conductivity of metal used and the thermal mass of the tube. The assembly is adapted to accomplish the temperature uniformity problem and the unheated lead problem without de-tuning the microwave field and/or causing an unsafe condition. Generally, the heated transfer line of this invention is designed to be heated to an elevated temperature between about 30° C. and about 500° C. The exact operating temperature is dependent on the nature of the sample, but generally the elevated temperature is between about 100° C. and about 450° C. In certain embodiments, the elevated temperature is between about 100° C. and about 400° C.

Suitable metals out of which the rod is made include, without limitation, copper (Cu), silver (Ag), aluminum (Al), gold (Au), antimony (Sb), zirconium (Zr), beryllium (Be), tungsten (W), molybdenum (Mo), alloys thereof, and mixtures or combinations thereof, where the term mixture means that the metals or metal alloys can be mixed to form homogeneous or heterogeneous mixtures and combinations means that the tube can be made up of sections or combinations of these metal or their alloys. The tube can also be made of section of these different metals. The alloys of these metals should have a thermal conductivity (W/m K) of at least 100 such as copper brass.

Figure 1:
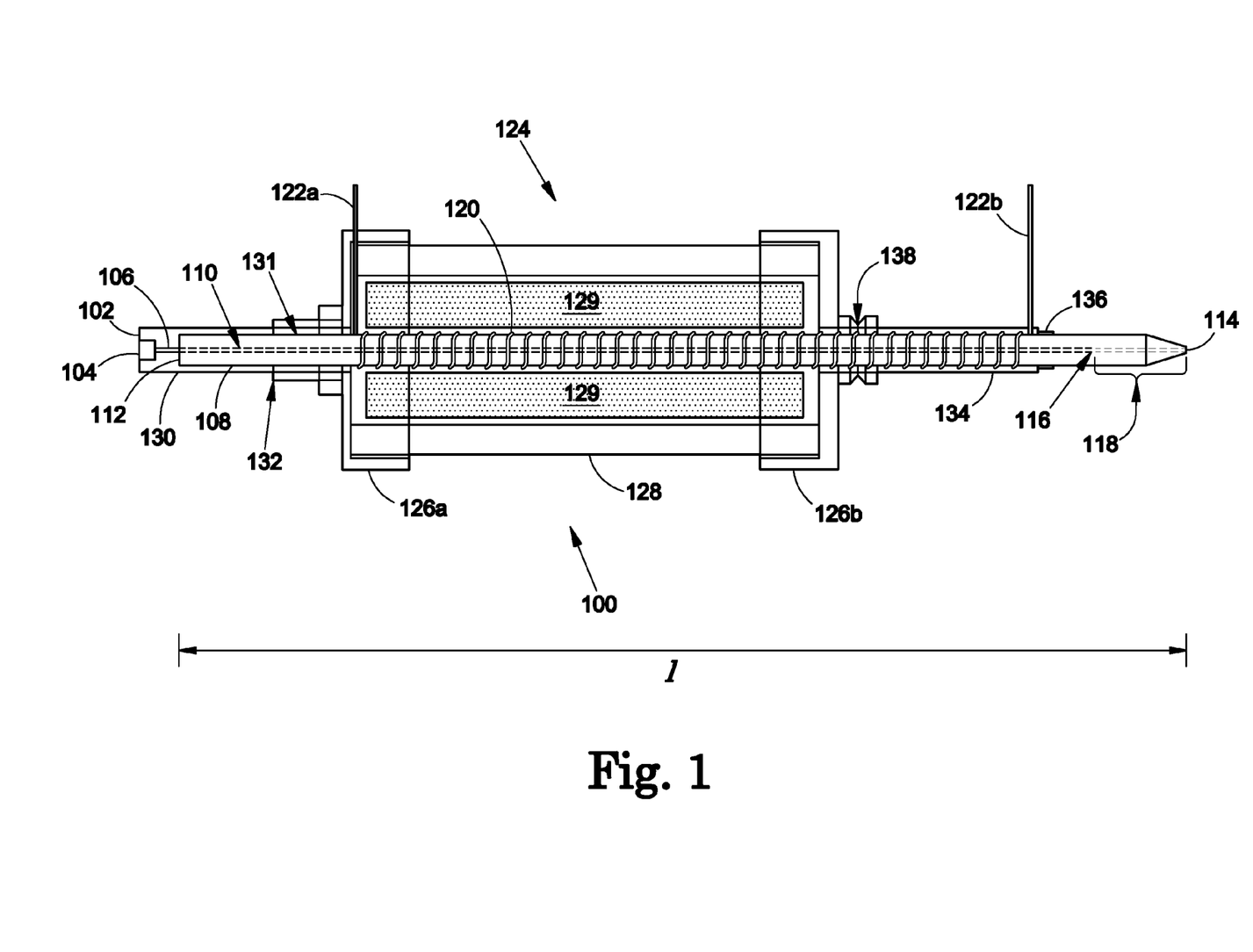
FIG. 1 depicts an embodiment of a heated transfer line apparatus of this invention.

Referring now to FIG. 1, an embodiment of a transfer line assembly, generally 100 is shown to include first end 102. The first end 102 includes a fitting 104 for connection to an injector, a sample loop or a detector (not shown) depending on whether the assembly is connecting a sample injector or loop to a column or a column to a detector. The assembly 100 also includes a transfer tube 106 and an elongated member or a rod 108 having a longitudinal aperture 110 therethrough. The rod 108 includes a first rod end 112 and a second rod end 114, where the second rod end 114 is also the second end of the assembly 100. The transfer tube 106 extends from the fitting 104 into the rod aperture 110 at its first end 112 and down a length 1 of the rod 108 to a position 116 near the second rod end 114. A portion 118 of the aperture 110 extending from the position 116 to the second rod end 114 is adapted to receive a column lead (not shown). The assembly 100 also includes a heating element 120 shown here as a wire wound around the rod 108 over a portion of its length 1 having element leads 122a&b. The assembly 100 also includes an insulating housing 124. The housing 124 includes first and second end caps 126a&b and a middle section 128, where the middle section 128 can include insulation 129. The housing 124 includes a proximal outwardly extending tube 130 designed to shield a proximal portion 131 of the rod 108, a portion 131 of the tube 106 between the fitting 104 and the proximal end 112 of the rod 108 and the fitting 104. The housing 124 also includes a proximate tightening fitting 132 for securing the first end cap 126a to the middle section 128. The housing 124 also includes a distal outwardly extending tube 134 having an end fitting 136, where the tube 134 is designed to shield a distal portion of the rod 108 and the heating element 120. The housing 124 also include a distal tightening fitting 138 for securing the second end cap 126b to the middle section 128. The distal end 114 of the rod 108 is designed to receive a column lead.

Figure 2A:
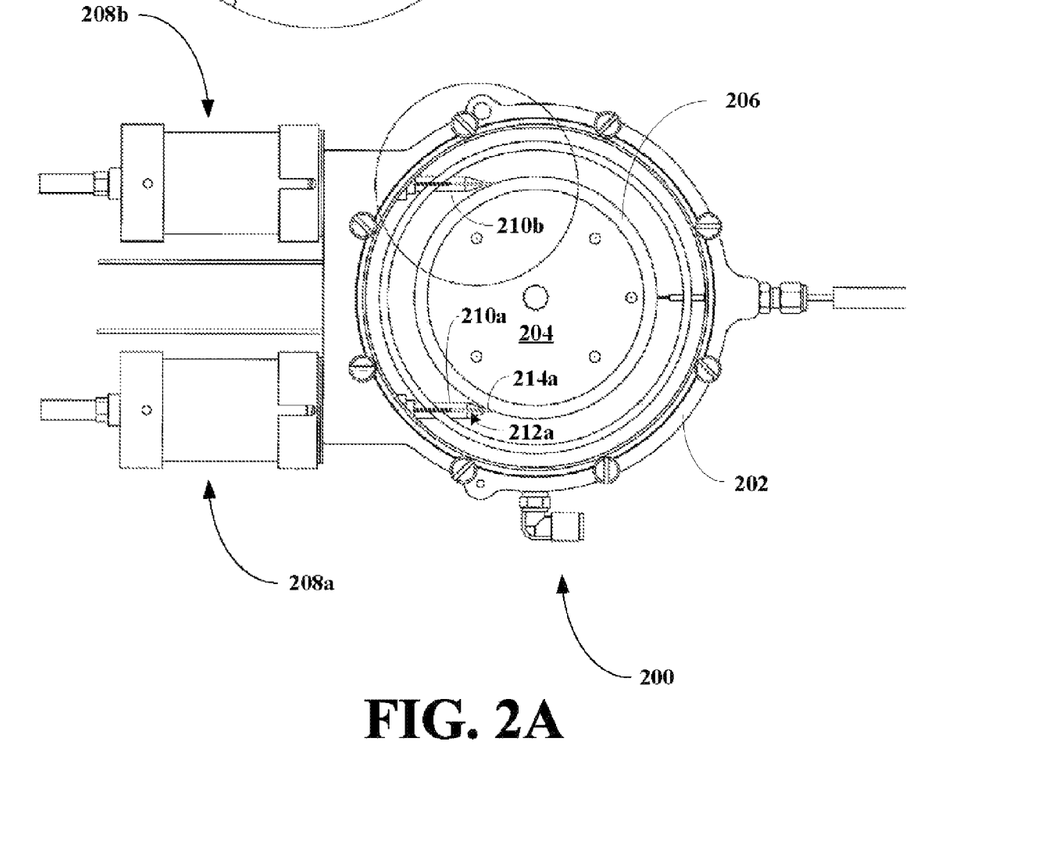
FIG. 2A depicts a microwave oven associated with a chromatography instrument of this invention equipped with heated transfer line apparatuses of FIG. 1.
Figure 2B:
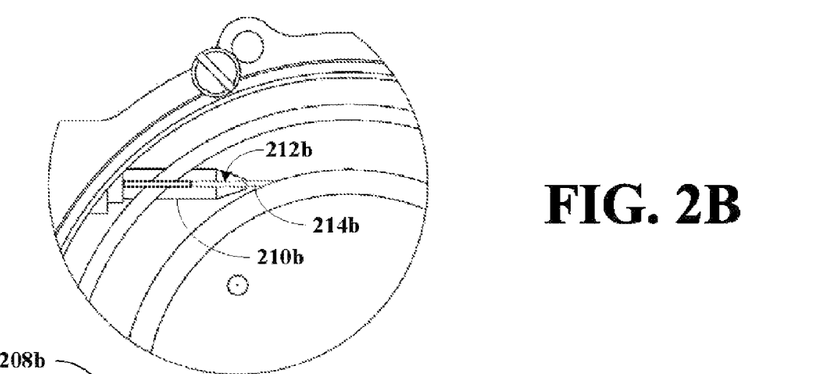
FIG. 2B depicts an expanded view of a section of the oven of FIG. 2A.

Referring now to FIGS. 2A&B, an embodiment of a microwave oven apparatus of this invention, generally 200, is shown to include a microwave oven housing 202, a heated zone 204, and a column 206 mounted within the heated zone 204. The apparatus 200 also includes an inlet transfer line assembly 208a and an outlet transfer line assembly 208b. The two transfer line assemblies 208a and 208b are as described in FIG. 1. The distal ends 210a&b of transfer line assemblies 208a&b are positioned into the microwave oven housing 202 so that an inlet column lead 212a and an outlet column lead 212b are inserted into the distal ends 210a&b of the assemblies 208a&b, respectively. The positioning of the distal ends 210a&b is sufficient to insure that unheated portions 214a&b of the leads 212a&b are less than 5 mm and to minimally interfere with the microwave field generated in the microwave oven.

Analytical Instruments

Figure 3A:
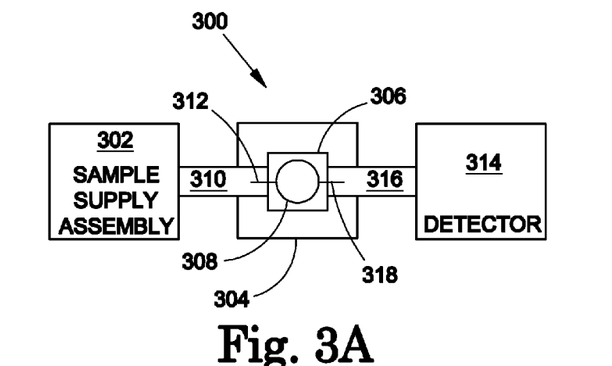
FIGS. 3A-C depict block diagram of a three embodiment of an analytical instrument of this invention.

Referring now to FIG. 3A, an embodiment of an instrument of this invention, generally 300, is shown to include a sample supply assembly 302 and a microwave oven apparatus 304 having a heating zone 306 including a chromatographic column 308. The system 300 also includes a first heated transfer line assembly 310 connecting the sample supply assembly 302 to an inlet column lead 312. The system 300 also includes a detection/analyzer assembly 314 and a second heated transfer line assembly 316 connecting an outlet column lead 318 to the detection/analyzer assembly 314. The sample supply assembly 302 can be a single port injector, an automated sample injector system, a sample loop, an in-line sample loop, an automated sample loop apparatus for forwarding numerous samples to the column, or any other sample supply assembly used in analytical instruments now or will be used in the future. The detector/analyzer assembly 314 can be any now know or yet to be developed oxide detection and analyzing system including, without limitation, IR spectrometers, FTIR spectrometers, MS spectrometers, UV spectrometers, UV fluorescence spectrometers, ICR spectrometers, any other spectrographic detection and analyzing system or mixtures or combinations thereof.

Figure 3B:
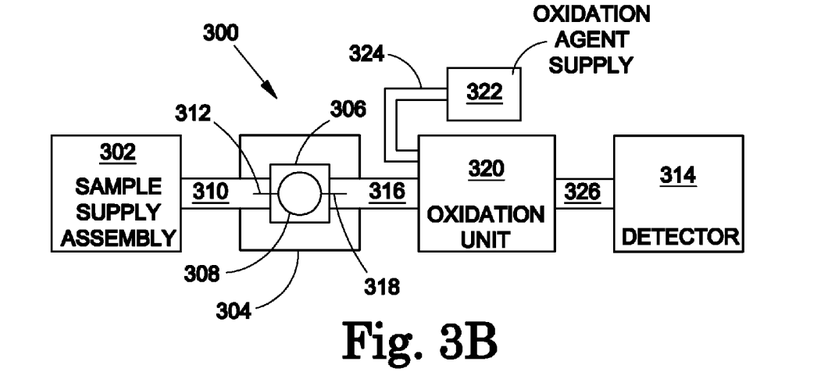

Referring now to FIG. 3B, another embodiment of an instrument of this invention, generally 300, is shown to include a sample supply assembly 302 and a microwave oven apparatus 304 having a heating zone 306 including a chromatographic column 308. The system 300 also includes a first heated transfer line assembly 310 connecting the sample supply assembly 302 to an inlet column lead 312. The system 300 also includes an oxidation unit 320 having an oxidizing agent supply 322 and a conduit 324 connecting the oxidizing agent supply 322 and the oxidation unit 320. The system 300 also includes a second heated transfer line assembly 316 connecting an outlet column lead 318 to the oxidation unit 320. The system 300 also includes a detection/analyzer assembly 314 and a third heated transfer line assembly 326 connecting the oxidation unit 320 to the detector/analyzer assembly 314. The second heated transfer line assembly 316 can also include a mixing or nebulizing unit (not shown) immediately upstream of the oxidation or combustion unit 320 adapted to supply a thoroughly mixed sample and oxidizing agent mixture to the combustion unit 320 or an atomized sample and oxidizing agent mixture to the combustion unit 320. If the assembly 326 includes a nebulizer, then the conduit 324 connects to the nebulizer as is well known in the art. The sample supply assembly 302 can be a single port injector, an automated sample injector system, a sample loop, an in-line sample loop, an automated sample loop apparatus for forwarding numerous samples to the column, or any other sample supply assembly used in analytical instruments now or will be used in the future. The detector/analyzer assembly 314 can be any now know or yet to be developed detector and analyzing system for oxides including, without limitation, IR spectrometers, FTIR spectrometers, MS spectrometers, UV spectrometers, UV fluorescence spectrometers, chemiluminescence spectrometers, ICR spectrometers, any other spectrographic detection and analyzing system or mixtures or combinations thereof. If the detection system includes a chemiluminescent detector, then detector will also include a source of ozone and associated conduits between the ozone generator and the detector.

Figure 3C:
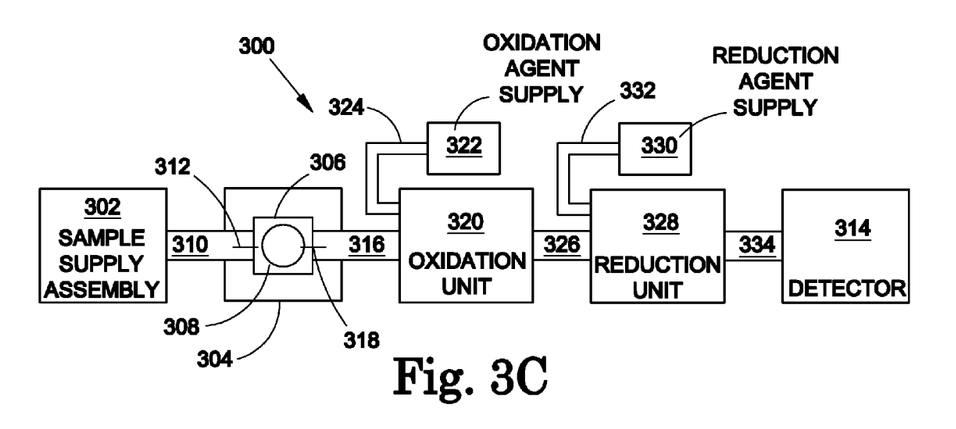

Referring now to FIG. 3C, another embodiment of an instrument of this invention, generally 300, is shown to include a sample supply assembly 302 and a microwave oven apparatus 304 having a heating zone 306 including a chromatographic column 308. The system 300 also includes a first heated transfer line assembly 310 connecting the sample supply assembly 302 to an inlet column lead 312. The system 300 also includes an oxidation unit 320 having an oxidizing agent supply 322 and a conduit 324 connecting the oxidizing agent supply 322 to the oxidation unit 320. The system 300 also includes a second heated transfer line assembly 316 connecting an outlet column lead 318 to the oxidation unit 320. The system 300 also includes a reduction unit 328 having a reducing agent supply 330 and a conduit 332 connecting the reducing agent supply 330 to the reduction unit 328. The system 300 also includes a third heated transfer line assembly 326 connecting the oxidation unit 310 to the reduction unit 328. The system 300 also includes a detection/analyzer assembly 314 and a fourth heated transfer line assembly 334 connecting the reduction unit 328 to the detector/analyzer assembly 314. The second heated transfer line assembly 316 can also include a mixing or nebulizing unit (not shown) immediately upstream of the oxidation or combustion unit 320 adapted to supply a thoroughly mixed sample and oxidizing agent mixture to the combustion unit 320 or an atomized sample and oxidizing agent mixture to the combustion unit 320. The sample supply assembly 302 can be a single port injector, an automated sample injector system, a sample loop, an in-line sample loop, an automated sample loop apparatus for forwarding numerous samples to the column, or any other sample supply assembly used in analytical instruments now or will be used in the future. The detector/analyzer assembly 314 can be any now know or yet to be developed detector and analyzing system for oxides including, without limitation, IR spectrometers, FTIR spectrometers, MS spectrometers, UV spectrometers, UV fluorescence spectrometers, chemiluminescence spectrometers, ICR spectrometers, any other spectrographic detection and analyzing system or mixtures or combinations thereof. If the detection system includes a chemiluminescent detector, then the detector will also include a source of ozone and associated conduits between the ozone generator and the detector.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A heated transfer line apparatus comprising:
    a housing including a proximal end cap, a distal end cap, a middle section, a proximal tubular member, and a distal tubular member, where the end caps fit on to the middle section to form an enclosed insulated zone, the proximal tubular member extends from the proximal end cap forming a first end of the apparatus and having a fitting adapted to connect to a sample introduction unit;
    an elongated member including a first end, a tapered second end and an aperture therethrough, where the elongated member is disposed inside the proximal tubular member, the middle section, and the distal tubular member and extends out of the distal tubular member so that the second end of the elongated member forms a second end of the apparatus;
    a transfer line extending from the fitting of the first end of the apparatus to a location near the second end of the apparatus; and
    a heating element surrounding the elongated member from the proximal end cap to the distal end of the distal tubular member and adapted to maintain the member and the transfer line at an elevated temperature substantially uniform therethrough with a variance of less than a set minimum temperature difference, the temperature being sufficient to maintain all components in a sample passing through the transfer line in their vapor or gas phase,
    where the tapered second end is adapted to be inserted into a microwave oven including a chromatography column and to receive a column end or column lead so that an unheated portion of the column is sufficiently small to reduce or eliminate sample condensation in the unheated portion of the column.

2. The apparatus of claim 1, wherein the unheated portion of the column is less than a critical distance.

3. The apparatus of claim 2, wherein the critical distance is 5mm or less.

4. The apparatus of claim 1, wherein the temperature is a minimum vaporization temperature of the sample.

5. The apparatus of claim 1, wherein the temperature is an elevated temperature between about 30° C. and about 500° C. and wherein the minimum temperature difference is no more than ±20° C.

6. The apparatus of claim 1, wherein the temperature is an elevated temperature between about 100° C. and about 400° C. and wherein the minimum temperature difference is no more than ±10° C.

7. The apparatus of claim 1, wherein the temperature is an elevated temperature between about 100° C. and about 400° C. and wherein the minimum temperature difference is no more than ±5° C.

8. The apparatus of claim 1, wherein the temperature is an elevated temperature between about 100 ° C. and about 400° C. and wherein the minimum temperature difference is no more than ±1° C.

9. The apparatus of claim 1, wherein the temperature is generally the minimum vaporization temperature of the sample.

10. The apparatus of claim 1, wherein the member has a thermal conductivity (W/mK) of at least 100.

11. The apparatus of claim 1, wherein the member comprises copper (Cu), silver (Ag), aluminum (Al), gold (Au), antimony (Sb), zirconium (Zr), beryllium (Be), tungsten (W), molybdenum (Mo), alloys thereof, and mixtures or combinations thereof.

12. The apparatus of claim 1, wherein the member comprises copper (Cu).

13. An oven apparatus comprising:
    a housing including a microwave heating assembly and a microwave heated zone;
    a chromatographic column disposed inside the microwave heated zone and including an inlet and outlet; and
    a first heated transfer line assembly and a second heated transfer line assembly, each assembly extending into the housing and adapted to receive the outlet and inlet so that there is no more than a critical distance of unheated column at either its outlet end or its inlet end,
    where each assembly comprises:
        an assembly housing including a proximal end cap, a distal end cap, a middle section, a proximal tubular member, and a distal tubular member, where the end caps fit on to the middle section to form an enclosed insulated zone, the proximal tubular member extends from the proximal end cap forming a first end of the apparatus and having a fitting adapted to connect to a sample introduction unit;

an elongated member including a first end, a tapered second end and an aperture therethrough, where the elongated member is disposed inside the proximal tubular member, the middle section, and the distal tubular member and extends out of the distal tubular member so that the second end of the elongated member forms a second end of the apparatus;

a transfer line extending from the fitting of the first end of the apparatus to a location near the second end of the apparatus; and a heating element surrounding the elongated member from the proximal end cap to the distal end of the distal tubular member and adapted to maintain the member and the transfer line at an elevated temperature substantially uniform therethrough with a variance of less than a set minimum temperature difference, the temperature being sufficient to maintain all components in a sample passing through the transfer line in their vapor or gas phase, where the tapered second end is adapted to be inserted into the oven apparatus housing including the chromatographic column and to receive a column end or column lead so that an unheated portion of the column is sufficiently small to reduce or eliminate sample condensation in the unheated portion of the column.

14. The apparatus of claim 13, wherein the unheated portion of the column is less than a critical distance.

15. The apparatus of claim 14, wherein the critical distance is 5 mm or less.

16. The apparatus of claim 13, wherein the temperature is a minimum vaporization temperature of the sample.

17. The apparatus of claim 13, wherein the temperature is an elevated temperature between about 30° C. and about 500° C. and the minimum temperature difference is no more than ±20° C.

18. The apparatus of claim 13, wherein the temperature is an elevated temperature between about 100° C. and about 400° C. and the minimum temperature difference is no more than ±10° C.

19. The apparatus of claim 13, wherein the temperature is an elevated temperature between about 100° C. and about 400° C. and the minimum temperature difference is no more than ±5° C.

20. The apparatus of claim 13, wherein the temperature is an elevated temperature between about 100° C. and about 400° C. and the minimum temperature difference is no more than ±1° C.

21. The apparatus of claim 13, wherein the temperature is generally the minimum vaporization temperature of the sample.

22. The apparatus of claim 13, wherein the member has a thermal conductivity (W/mK) of at least 100.

23. The apparatus of claim 13, wherein the member comprises copper (Cu), silver (Ag), aluminum (Al), gold (Au), antimony (Sb), zirconium (Zr), beryllium (Be), tungsten (W), molybdenum (Mo), alloys thereof, and mixtures or combinations thereof.

24. The apparatus of claim 13, wherein the member comprises copper (Cu).

25. A microwave heated chromatography instrument comprising:

a sample delivery assembly;

an oven apparatus connected to the sample delivery assembly, where the oven apparatus comprises:

a housing including a microwave heating assembly and a microwave heated zone;

a chromatographic column disposed inside the microwave heated zone and including an inlet and outlet;

a first heated transfer line assembly and a second heated transfer line assembly, each assembly extending into the housing and adapted to receive the outlet and inlet so that there is no more than a critical distance of unheated column at either its outlet end or its inlet end, where each assembly comprises:

an assembly housing including a proximal end cap, a distal end cap, a middle section, a proximal tubular member, and a distal tubular member, where the end caps fit on to the middle section to form an enclosed insulated zone, the proximal tubular member extends from the proximal end cap forming a first end of the assembly and having a fitting adapted to connect to a sample introduction unit;

an elongated member including a first end, a tapered second end and an aperture therethrough, where the elongated member is disposed inside the proximal tubular member, the middle section, and the distal tubular member and extends out of the distal tubular member so that the second end of the elongated member forms a second end of the assembly;

a transfer line extending from the fitting of the first end of the assembly to a location near the second end of the assembly; and a heating element surrounding the elongated member from the proximal end cap to the distal end of the distal tubular member and adapted to maintain the member and the transfer line at an elevated temperature substantially uniform therethrough with a variance of less than a set minimum temperature difference, the temperature being sufficient to maintain all components in a sample passing through the transfer line in their vapor or gas phase, where the tapered second end is adapted to be inserted into the oven apparatus housing including the chromatographic column and to receive a column end or column lead so that an unheated portion of the column is sufficiently small to reduce or eliminate sample condensation in the unheated portion of the column; and a detector/analyzer assembly connected to the distal end of the second transfer line and designed to detect and analyze components of the sample.

26. The instrument of claim 25, wherein the detector/analyzer assembly further includes an oxidation subassembly and/or reduction subassembly prior to the detector.

27. The instrument of claim 25, wherein the unheated portion of the column is less than a critical distance.

28. The instrument of claim 27, wherein the critical distance is 5 mm or less.

29. The instrument of claim 25, wherein the temperature is a minimum vaporization temperature of the sample.

30. The instrument of claim 25, wherein the temperature is an elevated temperature between about 30° C. and about 500° C. and the minimum temperature difference is no more than ±20° C.

31. The instrument of claim 25, wherein the temperature is an elevated temperature between about 100° C. and about 400° C. and the minimum temperature difference is no more than ±10° C.

32. The instrument of claim 25, wherein the temperature is an elevated temperature between about 100° C. and about 400° C. and the minimum temperature difference is no more than ±5° C.

33. The instrument of claim 25, wherein the temperature is an elevated temperature between about 100° C. and about 400° C. and the minimum temperature difference is no more than ±1° C.

34. The instrument of claim 25, wherein the temperature is generally the minimum vaporization temperature of the sample.

35. The instrument of claim 25, wherein the member has a thermal conductivity (W/mK) of at least 100.

36. The instrument of claim 25, wherein the member comprises copper (Cu), silver (Ag), aluminum (Al), gold (Au), antimony (Sb), zirconium (Zr), beryllium (Be), tungsten (W), molybdenum (Mo), alloys thereof, and mixtures or combinations thereof.

37. The instrument of claim 25, wherein the member comprises copper (Cu).

38. A method for increasing reliability of microwave heated chromatography instruments comprising the steps of:
providing a microwave heated chromatography instrument comprising:
a sample delivery assembly;
an oven apparatus connected to the sample delivery assembly,
where the oven apparatus comprises:
a housing including a microwave heating assembly and a microwave heated zone;
a chromatographic column disposed inside the microwave heated zone and including an inlet and outlet;
a first heated transfer line assembly and a second heated transfer line assembly, each assembly extending into the housing and adapted to receive the outlet and inlet so that there is no more than a critical distance of unheated column at either its outlet end or its inlet end,
where each assembly comprises:
an assembly housing including a proximal end cap, a distal end cap, a middle section, a proximal tubular member, and a distal tubular member, where the end caps fit on to the middle section to form an enclosed insulated zone, the proximal tubular member extends from the proximal end cap forming a first end of the assembly and having a fitting adapted to connect to a sample introduction unit;
an elongated member including a first end, a tapered second end and an aperture therethrough, where the elongated member is disposed inside the proximal tubular member, the middle section, and the distal tubular member and extends out of the distal tubular member so that the second end of the elongated member forms a second end of the assembly;
a transfer line extending from the fitting of the first end of the assembly to a location near the second end of the assembly; and
a heating element surrounding the elongated member from the proximal end cap to the distal end of the distal tubular member and adapted to maintain the member and the transfer line at an elevated temperature substantially uniform therethrough with a variance of less than a set minimum temperature difference, the temperature being sufficient to maintain all components in a sample passing through the transfer line in their vapor or gas phase,
where the tapered second end is adapted to be inserted into the oven apparatus housing including the chromatographic column and to receive a column end or column lead so that an unheated portion of the column is sufficiently small to reduce or eliminate sample condensation in the unheated portion of the column; and
a detector/analyzer assembly connected to the distal end of the second transfer line and designed to detect and analyze components of the sample;
maintaining the first transfer line at a first elevated temperature sufficient to maintain the sample in a vaporized state between the sample delivery assembly and the oven apparatus having a first temperature difference of no more that ±20° C.;
maintaining the second transfer line at a second elevated temperature sufficient to maintain the separated sample components in a vaporized state between the oven apparatus and the detector/analyzer assembly having a second temperature difference of no more that ±20° C.; and
detecting/analyzing the sample components.

39. The method of claim 38, further comprising the step of:
oxidizing the sample components to their corresponding oxides prior to detection and analysis.

40. The method of claim 38, further comprising the steps of:
oxidizing the sample components to their corresponding oxides; and
reducing a portion of the oxides to their corresponding reduced states prior to detection and analysis.

41. The method of claim 38, wherein the unheated portion of the column is less than a critical distance.

42. The method of claim 41, wherein the critical distance is 5 mm or less.

43. The method of claim 38, wherein the temperature is a minimum vaporization temperature of the sample.

44. The method of claim 38, wherein the temperature is an elevated temperature between about 30° C. and about 500° C. and the minimum temperature difference is no more than ±20° C.

45. The method of claim 38, wherein the temperature is an elevated temperature between about 100° C. and about 400° C. and the minimum temperature difference is no more than ±10° C.

46. The method of claim 38, wherein the temperature is an elevated temperature between about 100° C. and about 400° C. and the minimum temperature difference is no more than ±5° C.

47. The method of claim 38, wherein the temperature is an elevated temperature between about 100° C. and about 400° C. and the minimum temperature difference is no more than ±1° C.

48. The method of claim 38, wherein the temperature is generally the minimum vaporization temperature of the sample.

49. The method of claim 38, wherein the member has a thermal conductivity (W/mK) of at least 100.

50. The method of claim 38, wherein the member comprises copper (Cu), silver (Ag), aluminum (Al), gold (Au), antimony (Sb), zirconium (Zr), beryllium (Be), tungsten (W), molybdenum (Mo), alloys thereof, and mixtures or combinations thereof.

51. The method of claim 38, wherein the member comprises copper (Cu).

* * * * *